United States Patent [19]
Gilmore

[11] Patent Number: 5,185,361
[45] Date of Patent: Feb. 9, 1993

[54] PHARMACEUTICAL COMPOUNDS

[75] Inventor: Jeremy Gilmore, Frimley, Great Britain

[73] Assignee: Lilly Industries Limited, Besingstoke, United Kingdom

[21] Appl. No.: 761,587

[22] Filed: Sep. 18, 1991

[30] Foreign Application Priority Data

Sep. 18, 1990 [GB] United Kingdom ............... 9020338.1

[51] Int. Cl.$^5$ ................... A61K 31/405; C07D 209/10
[52] U.S. Cl. .................................. 514/415; 548/491; 548/503; 548/511
[58] Field of Search ................ 514/415; 548/491, 503, 548/511

[56] References Cited

FOREIGN PATENT DOCUMENTS

| | | |
|---|---|---|
| 0159376 | 10/1985 | European Pat. Off. . |
| 0179619 | 4/1986 | European Pat. Off. . |
| 0242167 | 10/1987 | European Pat. Off. . |
| 2238790 | 6/1991 | United Kingdom ................ 548/503 |

*Primary Examiner*—Joseph Paul Brust
*Assistant Examiner*—Jacqueline Haley
*Attorney, Agent, or Firm*—Donald G. Epple; Leroy Whitaker; John C. Demeter

[57] ABSTRACT

A pharmaceutical compound of the formula

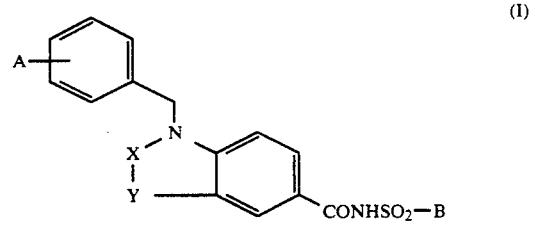

(I)

in which A is selected from $-NHCOR^1$, $-NHCOOR^1$, $-NHCONHR^1$, $-NHCSNHR^1$, $-CONHR^1$, where $R^1$ is optionally halo-substituted $C_{1-10}$ alkyl, $C_{2-10}$ alkenyl, $C_{3-7}$ cycloalkyl-$C_{1-4}$ alkyl or phenyl-$C_{1-4}$ alkyl B is optionally substituted phenyl, and $-X-Y-$ is $-CH=CH-$ or $-CH_2-CH_2-$; and salts thereof. The compounds are leukotriene antagonists.

7 Claims, No Drawings

PHARMACEUTICAL COMPOUNDS

The invention relates to pharmaceutical compounds, their use and preparation.

The compounds of the invention are of the formula

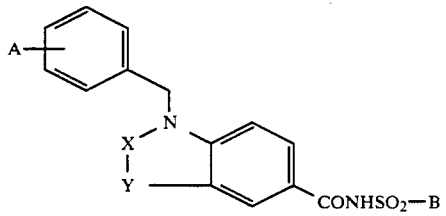

(I)

in which A is selected from —NHCOR$^1$, —NHCOOR$^1$, —NHCONHR$^1$, —NHCSNHR$^1$, —CONHR$^1$, where R$^1$ is optionally halo-substituted $C_{1-10}$ alkyl, $C_{2-10}$ alkenyl, $C_{3-7}$ cycloalkyl-$C_{1-4}$ alkyl or phenyl-$C_{1-4}$ alkyl, B is optionally substituted phenyl, and —X—Y— is —CH=CH— or —CH$_2$—CH$_2$—; and salts thereof.

The compounds of the invention and their pharmaceutically-acceptable salts are leukotriene antagonists and are indicated for use in the treatment of diseases in which leukotrienes are a causal mediator.

In the above formula, R$^1$ can be optionally halo-substituted $C_{1-10}$ alkyl, $C_{2-10}$ alkenyl, $C_{3-7}$ cycloalkyl-$C_{1-4}$ alkyl or phenyl-$C_{1-4}$alkyl. A $C_{1-10}$ alkyl or $C_{2-10}$ alkenyl group may be branched or unbranched and is preferably $C_{1-6}$ alkyl or $C_{2-6}$ alkenyl. Examples of the former include methyl, ethyl, propyl, isopropyl, butyl, isobutyl, sec. butyl and tert. butyl, and preferred examples of the latter are vinyl, allyl, propenyl, 2-methyl-2-propenyl and 2-methyl-3-butenyl. When the $C_{1-10}$ alkyl group is halo-substituted it can be substituted by one or more, such as for example 1 to 5, and especially three, halogen atoms, in particular, chloro, bromo and fluoro. Preferably the alkyl group comprises a trifluoromethyl group for instance in the terminal position. A $C_{3-7}$ cycloalkyl-$C_{1-4}$ alkyl group can be branched in the alkyl attachment, and is preferably of the form $C_{3-7}$ cycloalkyl-(CH$_2$)$_n$— where n is 1 to 4 and preferably 1. The cycloalkyl group can for example be cyclopropyl, cyclobutyl or cyclopentyl. A phenyl-$C_{1-4}$ alkyl group may be branched or unbranched in the alkyl attachment, and preferably is of the form phenyl-(CH$_2$)$_n$— where n is 1 to 4, a preferred instance being benzyl. R$^1$ is most preferably benzyl, $C_{1-4}$ alkyl or halo-substituted $C_{1-4}$ alkyl.

The group B is optionally substituted phenyl, and this is preferably phenyl or phenyl substituted with one or more, preferably one to three, substituents selected from $C_{1-4}$ alkyl, especially methyl, nitro, cyano, carboxyl, amino, hydroxyl, trifluoromethyl, $C_{1-4}$ alkoxy, especially methoxy and ethoxy, and halogen especially fluorine, chlorine or bromine. Preferably B is a phenyl ring substituted with a single substituent selected from $C_{1-4}$ alkyl, $C_{1-4}$ alkoxy and halogen, and especially at the ortho position.

The preferred values of A are —NHCOR$^1$, —NHCOOR$^1$, —NHCSNHR$^1$ and —NHCONHR$^1$, and the group is preferably at the meta position.

Thus a particular group of compounds according to the invention is of the formula

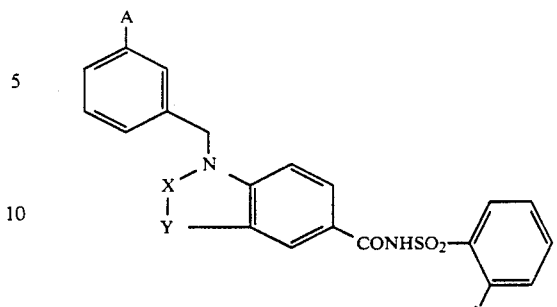

in which A is —NHCOR$^1$, —NHCOOR$^1$, —NHCSNR$^1$ or —NHCONHR$^1$, —X—Y— is —CH=CH— or —CH$_2$—CH$_2$—, and R$^3$ is $C_{1-4}$ alkyl, $C_{1-4}$ alkoxy or halogen.

As mentioned above, the compounds of the invention when basic or acidic in free form, can exist as salts. Nontoxic addition salts are included such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic acids for example methane sulphonic, ethane sulphonic, 2-hydroxyethane sulphonic, toluene-p-sulphonic, or naphthalene-2-sulphonic acid. Apart from pharmaceutically acceptable acid addition salts, other salts are also included within the scope of acid addition salts such as, for example, those with picric or oxalic acids; they may serve as intermediates in the purification of the compounds or in the preparation of other, for example pharmaceutically acceptable, acid addition salts, or are useful for identification, characterisation or purification of the bases. When the compounds of the invention contain an acid group, cationic salts can be prepared such as inorganic salts formed with alkali or alkaline earth metal metals especially sodium and potassium, or organic base salts such as ammonium or tetramethylammonium.

The invention also includes a process which comprises (i) reacting a compound of the formula

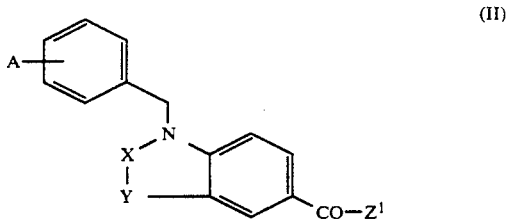

(II)

in which A, X and Y have the values given them above and Z$^1$ is a leaving group, with a sulphonamide of the formula BSO$_2$NH$_2$, or a salt thereof, to give a compound of formula (I), or (ii) converting a compound of the formula

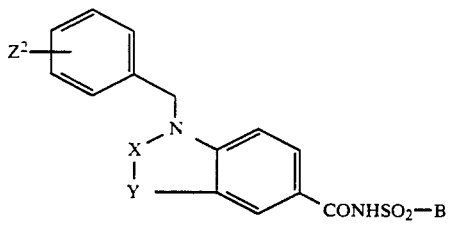

(III)

in which $Z^2$ is $-NH_2$ or $-CO_2H$, to a compound of formula (I) in which A is $-NHCOR^1$, $-NHCOOR^1$, $-NHCONHR^1$, $-NHCSNHR^1$ or $-CONHR^1$.

With regard to process (i), the reaction is preferably carried out at a temperature of from 0° C. to 150° C. and in the presence of an organic solvent, such as for example dichloromethane, toluene or tetrahydrofuran. Compounds of formula (II) bear a reactive $-CO-Z^1$ substituent, where $Z^1$ is a leaving group such as for example $-OZ^3$ where $Z^3$ is $C_{1-4}$ alkyl, or $-OH$ combined with an activating agent such as dicyclohexyl carbodiimide, 1-(3-dimethylaminopropyl)-3-ethyl carbodiimide, diphenyl carbamoyl chloride, or o-toluene sulphonyl isocyanate.

Formula (II) compounds can readily be prepared from known compounds by well known methods. Starting from a substituted fused ring compound of the formula

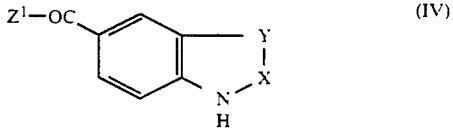

(IV)

the basic cyclic system is synthesised by reaction with

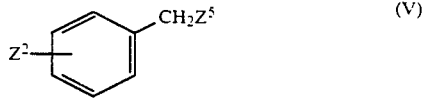

(V)

where $Z^2$ is a group selected from $-NO_2$, $-COZ^4$ or $-CN$, where $Z^4$ is $-OC_{1-4}$ alkyl and $Z^5$ is halo, to give the compound

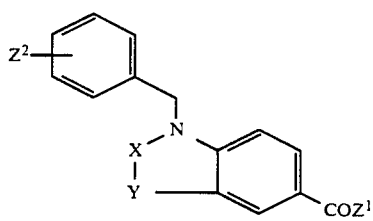

The $Z^2$ group can be converted to one of the desired values of A by conventional means. For example, when $Z^2$ is $-NO_2$ reduction to amine then reaction with acyl halide gives compounds in which A is $-NHCOR^1$ and with the chloroformate gives compounds in which A is $-NHCOOR^1$. Reaction of the amine with isocyanate or thiocyanate gives compounds in which A is $-NHCONHR^1$ and $-NHCSNHR^1$, respectively. Reaction of compounds in which $Z^2$ is $-COZ^4$ with amine yields compounds in which A is $-CONHR^1$.

The 5-carbomethoxy indoles of formula (IV) above are known compounds as are others of this type, and can, for example, be made by the procedure of Leimgruber and Batcho, Organic Synthesis Coll. Vol. V, 214-224. The indolines of formula (IV) above can, for example, be synthesised from the corresponding indoles by catalytic hydrogenation.

The compounds of the invention are pharmacologically active, being leukotriene antagonists as shown by the test of Fleisch et al. (J. Pharmacol. Exp. Ther., 233, 148-157). Isolated guinea pig tracheal strip was suspended in Krebs solution at 37° C. and aerated with 95% oxygen and 5% carbon dioxide. Concentration response curves to leukotriene ($LTC_4$ and $LTD_4$) were generated and the effects of different concentration of drug investigated. Dissociation constants ($K_B$) of the receptor inhibitor complex were calculated by the method of Furchgott (Furchgott R. F. Handbook of Experimental Pharmacology, New York, Vol. 33 pages 383-385). The compounds of the invention disclosed in the following Examples had a $pK_B$ of greater than 7. The compounds were also active in the total pulmonary resistance test (see Fleisch et al. above). Measurement of bronchospasm was recorded as an increase in tracheal resistance produced by $LTD_4$ administered intravenously into anaesthetised artificially ventilated guinea pigs. Also compounds of the invention are active in the in vivo Guinea Pig Pulmonary Function Test of Austen and Drazen (1974) J. Clin. Invest. 53, 1679-1685 at intravenous dosage levels of from 0.05 μg to 5.0 mg/kg and in a modified "Herxheimer" test (Journal of Physiology (London) 117, 251 (1952) at doses of from 25 to 200 mg/kg. The "Herxheimer" test is based on an $LTD_4$-induced bronchospasm in guinea pigs which closely resembles an asthmatic attack in man.

The compounds are accordingly indicated for therapeutic use in the treatment of diseases in which leukotrienes are implicated. These include allergic reactions of the pulmonary system in which leukotrienes are thought to be causal mediators of bronchospasm, for example, in allergic lung disorders such as extrinsic asthma and industrial asthmas such as Farmers lung, and in other inflammatory disorders, for example, associated with acute or chronic infectious diseases such as allergic skin diseases, ectopic and atopic eczemas, psoriasis, contact hypersensitivity and angioneurotic oedema, bronchitis and cystic fibrosis and rheumatic fever.

The compounds of the invention also have potential in the treatment of vascular diseases such as shock and ischaemic heart diseases for example coronary artery disease and myocardial infarction, cerebrovascular diseases, and renal diseases for example renal ischaemia.

Thus the invention also includes a pharmaceutical composition comprising a pharmaceutically acceptable diluent or carrier in association with a compound of formula (I) in unprotected form; or a pharmaceutically acceptable salt thereof.

The compounds may be administered by various routes, for example by the oral or rectal route, topically or parenterally, for example by injection or infusion, and especially by inhalation, being usually employed in the form of a pharmceutical composition. Such compositions are prepared in a manner well known in the pharmaceutical art and normally comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. The compounds of the invention are particularly suitable for administration by inhalation, in forms of presentation which include, for example, aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxybenzoate, talc magnesium stearate and mineral oil. The compositions of the injection may, as is well known in the art, be formulated so as to provide quick, sustained or delayed release of the active ingredient after administration to the patent.

Where the compositions are formulated in unit dosage form, it is preferred that each unit dosage form contains from 5 mg to 500 mg, for example, from 25 mg to 200 mg. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The invention is illustrated by the following Examples.

EXAMPLE 1

Methyl 1-(3-nitrobenzyl)indole-5-carboxylate

Methyl indole-5-carboxylate (10 g) was dissolved in dry tetrahydrofuran (250 ml) and cooled in an ice-bath. To the stirred solution was added sodium hydride (60% suspension in oil) (2.57 g) in portions over 15 minutes. After stirring for a further 30 minutes, 3-nitrobenzyl bromide (11.55 g) in dry tetrahydrofuran (30 ml) was added dropwise over 20 minutes. Stirring was continued at 0° C. for 30 minutes, then at room temperature for 2 hours. Excess sodium hydride was destroyed by cautious addition of acetic acid, then the reaction mixture extracted from brine into ethyl acetate, dried over anhydrous magnesium sulphate, filtered and evaporated in vacuo. Recrystallisation from ethyl acetate/hexane afforded methyl 1-(3-nitrobenzyl)indole-5-carboxylate (m.p. 129°–130° C.).

EXAMPLE 2

1-(3-Nitrobenzyl)indole-5-carboxylic acid

To a solution of the methyl ester (Example 1) (12.5 g) in tetrahydrofuran (150 ml) and methanol (300 ml) was added 2N sodium hydroxide (78 ml). The reaction mixture was heated under reflux for 4 hours, then cooled. The volume was reduced in vacuo to approximately 100 ml. and the solution acidified with 5N hydrochloric acid. On cooling, the crystalline product was filtered off and dried in vacuo in the oven at 50° C. to give 1-(3-nitrobenzyl)indole-5-carboxylic acid (m.p. 251°–254° C.).

EXAMPLE 3

N-[1-(3-nitrobenzyl)indol-5-ylcarbonyl]-2-methylbenzene sulphonamide

The carboxylic acid (Example 2) (6.2 g) was stirred at room temperature in dichloromethane (50 ml) with 2-methylbenzene sulphonamide (3.4 g), 1-(3-dimethylaminopropyl)-3-ethylcarbodiimide hydrochloride (4.6 g) and 4-dimethylaminopyridine (0.25 g) for 72 hours. The reaction mixture was diluted with dichloromethane and washed with 0.5N hydrochloric acid, then water. The organic extract was dried over anhydrous magnesium sulphate, filtered and evaporated in vacuo. Purification by flash chromatography on silica, eluting with 0–2% ethyl acetate in dichloromethane, afforded N-[1-(3-nitrobenzyl)indol-5-ylcarbonyl]-2-methylbenzene sulphonamide (m.p. 208°–210° C.).

EXAMPLE 4

N-[1-(3-aminobenzyl)indol-5-ylcarbonyl]-2-methylbenzene sulphonamide

The nitrobenzylindole (Example 3) (2.7 g) was dissolved in methanol (125 ml) and ethyl acetate (125 ml), and 10% palladium on charcoal (0.5 g) added. The reaction mixture was hydrogenated in a Parr bottle at 50 p.s.i. with shaking until hydrogen uptake was complete (approximately 1 hour). The catalyst was filtered off through Celite and the solvent removed in vacuo to give N-[1-(3-aminobenzyl)indol-5-ylcarbonyl]-2-methylbenzene sulphonamide as a foam. This crude product was used in the next step without purification.

EXAMPLE 5

N-{1-[3-(n-Butoxycarbonylamino)benzyl]indol-5-ylcarbonyl}-2-methylbenzene sulphonamide The amine (Example 4) (0.17 g) was dissolved in dichloromethane (5 ml) and 2,6-lutidine (50 μl) and stirred as n-butyl chloroformate (55 μl) was added over 2 minutes. The reaction mixture was stirred for 3 hours, diluted with dichloromethane and washed with 0.5N hydrochloric acid, then water. The organic extract was dried over anhydrous magnesium sulphate, filtered and evaporated in vacuo. Purification by flash chromatography on silica, eluting with 0–5% ethyl acetate in dichloromethane, yielded N-{1-[3-(n-butoxycarbonylamino)benzyl] indol-5-ylcarbonyl}-2-methylbenzene sulphonamide as a gum.

$^1$H NMR (DMSO-d$^6$, 300 MHz) δ0.89 (3H,t), 1.33 (2H,m), 1.56 (2H,m), 2.62 (3H,s), 4.02 (2H,t), 5.42 (2H,s), 6.66 (1H,d), 6.78 (1H,m), 7.19 (1H,t), 7.32 (1H,m), 7.35 (1H,m), 7.39 (1H,m), 7.46 (1H,m), 7.50 (1H,d), 7.58 (1H,m), 7.60 (1H,d), 7.63 (1H,dd), 8.05 (1H,dd), 8.28 (1H,d), 9.58 (1H,s), 12.4 (1H, bs).

EXAMPLES 6-16

Using a similar procedure to that described in Example 5, the amine (Example 4) was reacted with the appropriate chloroformate to give the following compounds:

EXAMPLE 6

N-{1-[3-(Iso-butoxycarbonylamino)benzyl]-indol-5-ylcarbonyl}-2-methylbenzene sulphonamide, m.p. 179°–181° C.

'H NMR (DMSO-d$^6$, 300 MHz) δ0.89 (6H,d), 1.86 (1H,m), 2.62 (3H,s), 3.81 (2H,d), 5.42 (2H,s), 6.65 (1H,d), 6.77 (1H,dd), 7.18 (1H,m), 7.31 (2H,m), 7.39 (1H,m), 7.43 (1H,m), 7.47 (1H,m), 7.55 (1H,m), 7.58 (1H,d), 7.62 (1H,dd), 8.03 (1H,dd), 8.26 (1H,d), 9.59 (1H,s).

EXAMPLE 7

N-{1-[3-(Benzyloxycarbonylamino)benzyl]indol-5-ylcarbonyl}-2-methylbenzene sulphonamide 'H NMR (DMSO-d$^6$, 300 MHz) δ2.62 (3H,s), 5.10 (2H,s), 5.42 (2H,s), 6.65 (1H,d), 6.78 (1H,m), 7.20 (1H,t), 7.32 (1H,m), 7.3–7.4 (7H), 7.45 (1H,m), 7.48 (1H,m), 7.54 (1H,m), 7.58 (1H,d), 7.64 (1H,dd), 8.03 (1H,dd), 8.26 (1H,d), 9.75 (1H,s).

EXAMPLE 8

N-{1-[3-(Cyclopentylmethoxycarbonylamino)benzyl]-indol-5-ylcarbonyl}-2-methylbenzene sulphonamide 'H NMR (CDCl$_3$, 300 MHz) δ1.5–1.8 (8H), 2.20 (1H,m), 2.75 (3H,s), 4.05 (2H,d), 5.30 (2H,s), 6.58 (1H,s), 6.65 (1H,d), 6.75 (1H,d), 7.2–7.6 (9H), 8.10 (1H,d), 8.30 (1H,dd), 8.85 (1H,bs).

EXAMPLE 9

N-{1-[3-(Cyclobutylmethoxycarbonylamino)benzyl]-indol-5-ylcarbonyl}-2-methylbenzene sulphonamide 'H NMR (CDCl$_3$, 300 MHz) δ1.75–2.10 (6H,m), 2.65 (1H,m), 2.70 (3H,s), 4.10 (2H,d), 5.30 (2H,s), 6.55 (1H,s), 6.65 (1H,d), 6.70 (1H,m), 7.15–7.6 (9H), 8.10 (1H,d), 8.30 (1H,dd), 8.65 (1H,bs).

EXAMPLE 10

N-{1-[3-(Cyclopropylmethoxycarbonylamino)benzyl]-indol-5-ylcarbonyl}-2-methylbenzene sulphonamide 'H NMR (CDCl$_3$, 300 MHz) δ0.30 (2H,m), 0.58 (2H,m), 1.13 (1H,m), 2.72 (3H,s), 3.96 (2H,d), 5.31 (2H,s), 6.57 (1H,s), 6.64 (1H,d), 6.74 (1H,m), 7.1–7.3 (6H), 7.41 (1H,m), 7.51 (1H,m), 7.59 (1H,m), 8.11 (1H,d), 8.28 (1H,dd), 8.71 (1H,bs).

EXAMPLE 11

N-{1-[3-(2-methylbutoxycarbonylamino)benzyl]-indol-5-ylcarbonyl}-2-methylbenzene sulphonamide 'H NMR (CDCl$_3$, 300 MHz) δ0.91 (3H), 0.92 (3H), 1.2–1.6 (2H,m), 1.70 (1H,m), 2.72 (3H,s), 3.9–4.1 (2H,m), 5.31 (2H,s), 6.54 (1H,s), 6.64 (1H,d), 6.72 (1H,d), 7.2–7.4 (6H), 7.42 (1H,m), 7.52 (1H,m), 7.58 (1H,dd), 8.10 (1H,d), 8.29 (1H,dd), 8.68 (1H,bs).

EXAMPLE 12

N-{1-[3-(2-methylbut-3-enyloxycarbonylamino)benzyl]indol-5-ylcarbonyl}-2-methylbenzene sulphonamide 'H NMR (CDCl$_3$, 300 MHz) δ1.04 (3H,d), 2.55 (1H,m), 2.70 (3H,s), 4.00 (2H,m), 5.05 (2H,m), 5.30 (2H,s), 5.75 (1H,m), 6.55 (1H,s), 6.65 (1H,d), 6.75 (1H,m), 7.15–7.3 (6H), 7.42 (1H,m), 7.50 (1H,m), 7.58 (1H,dd), 8.10 (1H,d), 8.30 (1H,dd), 8.75 (1H,bs).

EXAMPLE 13

N-{1-[3-(Isopropoxycarbonylamino)benzyl]-indol-5-ylcarbonyl}-2-methylbenzene sulphonamide 'H NMR (CDCl$_3$, 300 MHz) δ1.25 (6H,d), 2.70 (3H,s), 4.98 (1H,m), 5.30 (2H,s), 6.45 (1H,bs), 6.65 (1H,d), 6.75 (1H,m), 7.15–7.35 (6H), 7.41 (1H,m), 7.51 (1H,m), 7.56 (1H,dd), 8.10 (1H,d), 8.28 (1H,dd), 8.60 (1H,s).

EXAMPLE 14

N-{1-[3-(Propoxycarbonylamino)benzyl]indol-5-ylcarbonyl}-2-methylbenzene sulphonamide 'H NMR (CDCl$_3$, 300 MHz) δ0.95 (3H,t), 1.66 (2H,m), 2.72 (3H,s), 4.09 (2H,t), 5.30 (2H,s), 6.53 (1H,d), 6.64 (1H,d), 6.74 (1H,m), 7.2–7.4 (6H), 7.40 (1H,m), 7.49 (1H,m), 7.57 (1H,dd), 8.11 (1H,s), 8.31 (1H,d), 8.65 (1H,bs).

EXAMPLE 15

N-{1-[3-(1-Methylpropoxycarbonylamino)benzyl]-indol-5-ylcarbonyl}-2-methylbenzene sulphonamide 'H NMR (CDCl$_3$, 300 MHz) δ0.92 (3H,t), 1.24 (3H,d), 1.58 (2H,m), 2.72 (3H,s), 4.81 (1H,m), 5.31 (2H,s), 6.49 (1H,s), 6.65 (1H,m), 6.72 (1H,m), 7.2–7.3 (6H), 7.42 (1H,t), 7.51 (1H,m), 7.58 (1H,m), 8.11 (1H,d), 8.29 (1H,dd), 8.62 (1H,s).

EXAMPLE 16

N-{1-[3-(2-Methyl-2-propenyloxycarbonylamino)benzyl]indol-5-ylcarbonyl}-2-methylbenzene sulphonamide 'H NMR (CDCl$_3$, 300 MHz) δ1.77 (3H,s), 2.72 (3H,s), 3.5 (1H,b), 4.56 (2H,s), 4.94 (1H,bs), 4.99 (1H,bs), 5.31 (2H,s), 6.60 (1H,bs), 6.65 (1H,d), 6.74 (1H,dd), 7.2–7.6 (8H,m), 8.10 (1H,d), 8.29 (1H,d), 8.61 (1H,s).

EXAMPLE 17

N-{1-[3-(1-Methyl-2,2,2-trifluoroethoxycarbonylamino)benzyl]-indol-5-ylcarbonyl}-2-methylbenzene sulphonamide 'H NMR (CDCl$_3$, 300 MHz) δ1.45 (3H,d), 2.72 (3H,s), 3.5 (1H,b), 5.30 (1H,m), 5.34 (2H,s), 6.68 (2H,m), 6.80 (1H,m), 7.18 (1H,m), 7.2–7.35 (4H), 7.42 (1H,m), 7.50 (1H,m), 7.60 (1H,dd), 8.12 (1H,d), 8.30 (1H,dd), 8.65 (1H,bs).

EXAMPLE 18

N-{1-[3-(2-Methyl-3,3,3-trifluoropropoxycarbonylamino)benzyl]-indol-5-ylcarbonyl}-2-methylbenzene sulphonamide 'H NMR (CDCl$_3$, 300 MHz) δ1.70 (3H,d), 2.58 (1H,m), 2.71 (3H,s), 4.17 (1H,dd), 4.38 (1H,dd), 5.30 (2H,s), 6.63 (1H,s), 6.65 (1H,dd), 6.75 (1H,d), 7.10–7.35 (6H,m), 7.42 (1H,t), 7.50 (1H,dt), 7.58 (1H,dd), 8.12 (1H,d), 8.28 (1H,dd), 8.8 (1H,b).

EXAMPLE 19

N-{1-[3-(2,2,3,3,3,-Pentafluoropropoxycarbonylamino)benzyl]-indol-5-ylcarbonyl}-2-methylbenzene sulphonamide 'H NMR (CDCl$_3$, 300 MHz) δ2.72 (3H,s), 4.60 (2H,t), 5.30 (2H,s), 6.64 (1H,d), 6.80 (2H,m), 7.15 (1H,s), 7.21 (1H,d), 7.25-7.30 (4H,m), 7.40 (1H,t), 7.51 (1H,dt), 7.60 (1H,dd), 8.13 (1H,d), 8.29 (1H,dd).

EXAMPLE 20

Methyl 1-[3-(cyclopentyloxycarbonylamino)benzyl]-indole-5-carboxylate

The nitrobenzylindole (Example 1) (0.64 g) was dissolved in methanol (50 ml) and 10% palladium on charcoal (0.1 g) added. The reaction mixture was hydrogenated in a Parr bottle at 50 p.s.i. with shaking until hydrogen uptake was complete (approximately 1hour). The catalyst was filtered off through Celite and the solvent removed in vacuo.

The crude amine was dissolved in dichloromethane (15 ml) and 2,6-lutidine (0.22 g), and cooled in an ice-bath. Cyclopentyl chloroformate (0.31 g) in dichloromethane (1 ml) was added dropwise to the stirred solution over 2 minutes. After stirring for 10 minutes at 0° C., the ice-bath was removed and the reaction mixture stirred for a further 2 hours at room temperature. The solvent was removed in vacuo and the crude product purified by flash chromatography on silica, eluting with 25% ethyl acetate in hexane, to give methyl 1-[3-(cyclopentyloxycarbonylamino)benzyl]-indole-5-carboxylate, m.p. 131°-133° C.

EXAMPLE 21

N-{1-[3-(Cyclopentyloxycarbonylamino)benzyl]-indol-5-ylcarbonyl}-2-methylbenzene sulphonamide To a solution of the methyl ester (Example 20) (0.7 g) in tetrahydrofuran (8 ml) and methanol (4 ml) was added 2N lithium hydroxide (1.7 ml), and the reaction mixture heated under reflux for 3 hours. The cooled solution was acidified with 2N hydrochloric acid and the product extracted into chloroform. The organic extracts were dried over anhydrous magnesium sulphate, filtered and evaporated in vacuo.

The crude carboxylic acid was stirred at room temperature in dichloromethane (7 ml) with 2-methylbenzene sulphonamide (0.27 g), 1-(3-dimethylaminopropyl)-3-ethylcarbodiimide hydrochloride (0.37 g) and 4-dimethylaminopyridine (0.1 g) for 48 hours. The reaction mixture was diluted with dichloromethane and washed with 0.5N hydrochloric acid, then water. The organic extract was dried over anhydrous magnesium sulphate, filtered and evaporated in vacuo. Purification by flash chromatography on silica, eluting with 50-80% diethyl ether in 40°-60° C. petroleum ether, followed by crystallisation from dichloromethane/60°-80° C. petroleum ether afforded N-{1-[3-(cyclopentyloxycarbonylamino)-benzyl]-indol-5-ylcarbonyl}-2-methylbenzene sulphonamide, m.p. 188°-190° C.

'H NMR (CDCl$_3$, 300 MHz) δ1.69 (8H,m), 2.72 (3H,s), 5.15 (1H,s), 5.28 (2H,s), 6.60 (2H,m), 6.70 (1H,m), 7.1-7.4 (6H), 7.43 (1H,t), 7.51 (1H,m), 7.60 (1H,m), 8.13 (1H,s), 8.30 (1H,d), 9.00 (1H,s).

EXAMPLE 22

N-{1-[3-(3-Methylbutylcarbonylamino)benzyl]indol-5-ylcarbonyl}-2-methylbenzene sulphonamide A mixture of the amine (Example 4) (0.25 g), 3-methylvaleric acid (0.07 g), 1-(3-dimethylaminopropyl)-3-ethylcarbodiimide hydrochloride (0.126 g) and 4-dimethylaminopyridine (0.02 g) in dichloromethane (5 ml) was stirred at room temperature for 96 hours. The reaction mixture was washed with water then saturated brine, dried over anhydrous magnesium sulphate, filtered and evaporated in vacuo. Purification by flash chromatography on silica, eluting with 0-30% ethyl acetate in hexane, afforded N-{1-[3-(3-methylbutylcarbonylamino)benzyl]indol-5-ylcarbonyl}-2-methylbenzene sulphonamide.

'H NMR (CDCl$_3$, 300 MHz) δ0.91 (6H,d), 1.58 (1H,m), 1.55 (2H,m), 2.30 (2H,m), 2.71 (3H,s), 5.31 (2H,s) 6.63 (1H,d), 6.78 (1H,d), 7.09 (1H,s), 7.2-7.4 (6H), 7.41 (1H,t), 7.51 (1H,m), 7.56 (1H,m), 8.09 (1H,d), 8.28 (1H,dd), 8.73 (1H,s).

EXAMPLE 23

N-{1-[3-(Butylcarbonylamino)benzyl]indol-5-ylcarbonyl}-2-methylbenzene sulphonamide Using a similar procedure to that described in Example 22, the amine (Example 4) was reacted with butyric acid to give N-{1-[3-(butylcarbonylamino)benzyl]indol-5-ylcarbonyl}-2-methylbenzene sulphonamide.

'H NMR (CDCl$_3$, 300 MHz) δ0.90 (3H,t), 1.35 (2H,m), 1.63 (2H,m), 2.28 (2H,t), 2.70 (3H,s), 5.27 (2H,s), 6.60 (1H,d), 6.77 (1H,d), 7.1-7.6 (10H), 8.08 (1H,s), 8.27 (1H,d), 8.9 (1H,bs).

EXAMPLE 24

N-{1-[3-(3-Methyl-1-butenylcarbonylamino)benzyl]indol-5-ylcarbonyl}-2-methylbenzene sulphonamide Using a similar procedure to that described in Example 22, the amine (Example 4) was reacted with 3-methyl-1-butenoic acid to give N-{1-[3-(3-methyl-1-butenylcarbonylamino)-benzyl]indol-5-ylcarbonyl}-2-methylbenzene sulphonamide.

'H NMR (CHCl$_3$, 300 MHz) δ1.00 (3H,s), 1.03 (3H,s), 2.45 (1H,m), 2.62 (3H,s), 5.45 (2H,s), 6.00 (1H,dd), 6.66 (1H,dd), 6.75 (1H,dd), 6.87 (1H,d), 7.23 (1H,t), 7.4-7.6 (8H,m), 8.20 (1H,d), 8.27 (1H,dd), 9.92 (1H,s).

EXAMPLE 25

N-{1-[3-(3-Propyl-1-ureido)benzyl]indol-5-ylcarbonyl}-2-methylbenzene sulphonamide A mixture of the amine (Example 4) (0.25 g) and n-propyl isocyanate (0.051 g) in dichloromethane (5 ml) was stirred at room temperature for 24 hours. The reaction mixture was washed with water then saturated brine, dried over magnesium sulphate, filtered and evaporated in vacuo. Purification by flash chromatography on silica (eluant 0-100% ethyl acetate in hexane), followed by preparative reverse phase HPLC (1 inch LP1-ODS column; 60:40:0.1 methanol:water:acetic acid) gave N-{1-[3-(3-propyl-1-ureido)benzyl]indol-5-ylcarbonyl}-2-methylbenzene sulphonamide.

'H NMR (CDCl$_3$, 300 MHz) δ0.82 (3H,t), 1.41 (2H,m), 2.72 (3H,s), 3.03 (2H,m), 3.49 (1H,s), 4.8 (1H,bs), 5.22 (2H,s), 6.50 (2H,m), 6.75 (1H,m), 7.0-7.3 (5H), 7.3-7.5 (3H), 8.03 (1H,d), 8.27 (1H,dd), 9.3 (1H,bs).

EXAMPLE 26

N-{1-[3-(3-Isobutyl-1-thioureido)benzyl]indol-5-ylcarbonyl}-2-methylbenzene sulphonamide A mixture of the amine (Example 4) (0.35 g) and isobutyl isothiocyanate (0.116 g) in dichloromethane (5 ml) was stirred at room temperature for 72 hours, then heated under reflux for 4 hours. The reaction mixture was washed with water then saturated brine, dried over anhydrous magnesium sulphate, filtered and evaporated in vacuo. Purification by flash chromatography on silica (eluant 20–40% ethyl acetate in hexane), followed by preparative reverse-phase HPLC (1 inch LP1-ODS column; 60:40:0.1 methanol:water:acetic acid), gave N-{1-[3-(3-isobutyl-1-thioureido)benzyl]indol-5-ylcarbonyl}-2-methylbenzene sulphonamide.

$^1$H NMR (CDCl$_3$, 300 MHz) δ0.88 (6H,d), 1.75 (1H,m), 2.70 (3H,s), 3.30 (2H,t), 5.35 (2H,s), 5.9 (1H,bs), 6.65 (1H,d), 6.75 (1H,d), 7.0–7.6 (8H), 7.62 (1H,dd), 8.10 (1H,d), 8.30 (1H,dd).

EXAMPLE 27

N-{1-[3-(3-Propyl-1-thioureido)benzyl]indol-5-ylcarbonyl}-2-methylbenzene sulphonamide Using a similar procedure to that described in Example 26, the amine (Example 4) was reacted with propyl isothiocyanate to give N-{1-[3-(3-propyl-1-thioureido)benzyl]indol-5-ylcarbonyl}-2-methylbenzene sulphonamide.

$^1$H NMR (CDCl$_3$, 300 MHz) δ0.89 (3H,t), 1.43 (2H,m), 2.71 (3H,s), 3.45 (2H,q), 5.36 (2H,s), 5.84 (1H,bs), 6.68 (1H,d), 6.74 (1H,s), 7.05 (1H,dd), 7.12 (1H,dd), 7.24 (1H,d), 7.3–7.5 (4H), 7.5–7.6 (2H), 7.61 (1H,dd), 8.12 (1H,d), 8.30 (1H,dd).

EXAMPLE 28

1-[3-(Isobutoxycarbonylamino)benzyl]indole-5-carboxylic acid

The nitrobenzylindole (Example 2) (3 g) was dissolved in methanol (100 ml) and tetrahydrofuran (100 ml), and 10% palladium on charcoal (0.25 g) added. The reaction mixture was hydrogenated in a Parr bottle at 60 p.s.i. with shaking until hydrogen uptake was complete. The catalyst was filtered off through Celite and the solvent removed in vacuo.

The crude amine was dissolved in tetrahydrofuran (100 ml) and sodium bicarbonate (1.63 g) in water (15 ml) added. The reaction mixture was stirred as isobutyl chloroformate (1.59 g) was added dropwise over 5 minutes. Stirring was continued for 2 hours, then the reaction was acidified with acetic acid and extracted from saturated brine into ethyl acetate. The organic extracts were dried over anhydrous magnesium sulphate, filtered and evaporated in vacuo. Recrystallization from ethyl acetate/hexane afforded 1-[3-(isobutoxycarbonylamino)benzyl]-indole-5-carboxylic acid, m.p. 173°–176° C.

EXAMPLE 29

N-{1-[3-(Isobutoxycarbonylamino)benzyl]indol-5-ylcarbonyl}-benzene sulphonamide

The carboxylic acid (Example 28 ) (0.25 g) was stirred at room temperature in dichloromethane (3 ml) with benzene sulphonamide (0.10 g), 1-(3-dimethylaminopropyl)-3-ethylcarbodiimide hydrochloride (0.15 g) and 4-dimethylaminopyridine (0.02 g) for 144 hours. The reaction mixture was diluted with chloroform and washed with 0.5N hydrochloric acid, then water. The organic extract was dried over anhydrous magnesium sulphate, filtered and evaporated in vacuo. Purification by preparative reverse-phase HPLC (1 inch LP1-ODS column), eluting with 75:25:0.1 methanol:water:acetic acid, gave N-{1-[3-(isobutoxycarbonylamino)benzyl]indol-5-ylcarbonyl}benzene sulphonamide.

$^1$H NMR (DMSO, 300 MHz) δ0.89 (6H,d), 1.87 (1H,m), 3.82 (2H,d), 5.41 (2H,s) 6.63 (1H,d), 6.77 (1H,d), 7.19 (1H,t), 7.32 (2H,m), 7.45 (1H,d), 7.5–7.7 (6H), 7.98 (2H,m), 8.22 (1H,d), 9.60 (1H,s).

EXAMPLE 30

N-{1-[3-(Isobutoxycarbonylamino)benzyl]indol-5-ylcarbonyl}-2-chlorobenzene sulphonamide Using a similar procedure to that described in Example 29, the carboxylic acid (Example 28) was reacted with 2-chlorobenzene sulphonamide to give N-{1-[3-(isobutoxycarbonylamino)benzyl]indol-5-ylcarbonyl}-2-chlorobenzene sulphonamide.

$^1$H NMR (DMSO-d$^6$, 300 MHz) δ0.90 (6H,d), 1.85 (1H,m), 3.82 (2H,d), 5.42 (2H,s), 6.65 (1H,d), 6.78 (1H,d), 7.18 (1H,m), 7.30 (2H,m), 7.50 (1H,d), 7.58 (1H,d), 7.6–7.75 (5H), 8.18 (1H,dd), 8.30 (1H,d), 9.65 (1H,s).

EXAMPLE 31

Methyl indoline-5-carboxylate

Methyl indole-5-carboxylate (5 g) was dissolved in methanol (300 ml) containing concentrated sulphuric acid (12 ml) and 10% palladium on charcoal (1.0 g) added. The reaction mixture was hydrogenated in a Parr bottle at 65 p.s.i. with shaking for 48 hours. The catalyst was filtered off through Celite. The solution was made basic by addition of ammonia solution (0.880) and evaporated in vacuo. The product was extracted from water into ethyl acetate, the organic extracts dried over anhydrous magnesium sulphate, filtered and evaporated in vacuo to give methyl indoline-5-carboxylate, m.p. 70°–72° C.

EXAMPLE 32

Methyl 1-(3-nitrobenzyl)indoline-5-carboxylate

A mixture of the indoline (Example 31) (4.39 g), 3-nitrobenzyl bromide (5.02 g) and anhydrous potassium carbonate (3.17 g) in methylethylketone (150 ml) was heated under reflux for 18 hours. On cooling, the inorganics were filtered off and the solvent removed in vacuo. The reaction mixture was extracted from water into ethyl acetate, dried over anhydrous magnesium sulphate, filtered and evaporated in vacuo. Purification by flash chromatography on silica, eluting with chloroform, gave methyl 1-(3-nitrobenzyl)indoline-5-carboxylate, m.p. 99°–100° C.

EXAMPLE 33

1-(3-Nitrobenzyl)indoline-5-carboxylic acid

A suspension of the methyl ester (Example 32) (5.72 g) in 2N sodium hydroxide (35 ml) and methanol (140 ml) was heated under reflux for 6 hours. The reaction mixture was cooled and concentrated in vacuo. Acidification with aqueous hydrochloric acid and filtration gave 1-(3-nitrobenzyl)indoline-5-carboxylic acid, m.p. 259°–262° C.

EXAMPLE 34

N-[1-(3-Nitrobenzyl)indolin-5-ylcarbonyl]-2-methylbenzene sulphonamide

A mixture of the carboxylic acid (Example 33) (0.5 g), 2-methylbenzene sulphonamide (0.28 g), 1-(3-dimethylaminopropyl)-3-ethyl-carbodiimide hydrochloride (0.37 g) and 4-dimethylaminopyridine (0.05 g) in dichloromethane (6 ml) was stirred at room temperature for 72 hours. The reaction mixture was diluted with dichloromethane and washed with water and brine. The organic phase was dried over anhydrous magnesium sulphate, filtered and evaporated in vacuo. Purification by flash chromatography on silica, eluting with 0-2% ethyl acetate in dichloromethane, gave a yellow oil which, on crystallisation from methanol, afforded N-[1-(3-nitrobenzyl)indolin-5-ylcarbonyl]-2-methylbenzene sulphonamide, m.p. 159°-163° C.

EXAMPLE 35

N-{1-[3-(Isobutoxycarbonylamino)benzyl]-indolin-5-ylcarbonyl}-2-methylbenzene sulphonamide The nitrobenzylindoline (Example 34) (0.35 g) was dissolved in ethyl acetate (50 ml) and 10% palladium on charcoal (0.1 g) added. The reaction mixture was hydrogenated in a Parr bottle at 50 p.s.i. with shaking until hydrogen uptake was complete. The catalyst was filtered off through Celite and the solvent removed in vacuo.

The crude amine was dissolved in dichloromethane (15 ml) and 2,6-lutidine (90 µl), and cooled in an ice-bath. Isobutyl chloroformate (0.11 g) in dichloromethane (5 ml) was added dropwise to the stirred solution over 5 minutes. The ice-bath was removed and the reaction mixture stirred for a further 3.5 hours at room temperature. The solution was washed with aqueous hydrochloric acid, water and saturated brine. The organic phase was dried over anhydrous magnesium sulphate, filtered and evaporated in vacuo. An initial purification was carried out by flash chromatography on silica, eluting with 2.5-7.5% ethyl acetate in dichloromethane. Further purification by preparative reverse-phase HPLC (1 inch LP1-ODS column), eluting with methanol:water:acetic acid (70:30:0.1), gave N-{1-[3-(isobutoxycarbonylamino)benzyl]-indolin-5-ylcarbonyl}-2-methylbenzene sulphonamide.

$^1$H NMR (CDCl$_3$, 300 MHZ) δ0.95 (6H, d), 1.96 (1H, m), 2.69 (3H, s), 3.02 (2H, t), 3.54 (2H, t), 3.93 (2H, d), 4.34 (2H, s), 6.35 (1H, d), 6.66 (1H, s), 6.94 (1H, m), 7.25-7.45 (4H), 7.45-7.55 (3H), 8.25 (1H, dd), 8.7 (1H, bs).

The following formulations illustrate the invention.

EXAMPLE 36

Soft Gelatin Capsule

Each soft gelatin capsule contains:

| Active ingredient | 150 mg |
|---|---|
| Arachis oil | 150 mg |

After mixing together, the blend is filled into soft gelatin capsules using the appropriate equipment.

EXAMPLE 37

Hard Gelatin Capsule

Each capsule contains:

| Active ingredient | 50 mg |
|---|---|
| PEG 4000 | 250 mg |

The PEG 4000 is melted and mixed with the active ingredient. Whilst still molten the mixture is filled into capsule shells and allowed to cool.

EXAMPLE 38

| Aerosol | |
|---|---|
| Active ingredent | 10 mg |
| Ethanol | 50 mg |
| Dichlorodifluoromethane (Propellant 12) | 658 mg |
| Dichlorotetrafluoroethane (Propellant 14) | 282 mg |

The active ingredient is dissolved in the ethanol. The concentrate is filled into extruded aluminium cans for inhalation aerosols. The cans are degassed with propellant 12 and sealed with an appropriate metered dose valve. The volume of product expelled per actuation is 50 to 100 µl equivalent to 0.5-1 mg active ingredient.

I claim:

1. A compound of the formula

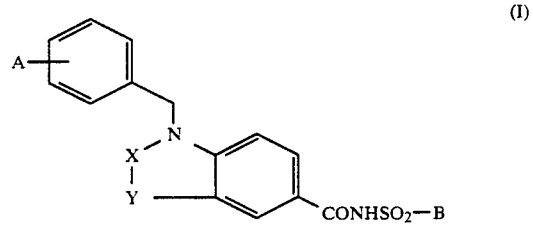

(I)

in which A is selected from —NHCOR$^1$, —NHCOOR$^1$, —NHCONHR$^1$, —NHCSNHR$^1$, —CONHR$^1$, where R$^1$ is optionally halo-substituted C$_{1-10}$ alkyl, C$_{2-10}$ alkenyl, C$_{3-7}$ cycloalkyl-C$_{1-4}$ alkyl or phenyl-C$_{1-4}$ alkyl, B is optionally substituted phenyl, and —X—Y— is —CH=CH— or —CH$_2$—CH$_2$—; or a salt thereof.

2. A compound according to claim 1, in which A is —NHCOR$^1$, —NHCOOR$^1$, —NHCSNHR$^1$ or —NHCONHR$^1$.

3. A compound according to claim 2, in which R$^1$ is benzyl, C$_{1-4}$ alkyl or halo-substituted C$_{1-4}$ alkyl.

4. A compound according to claim 3, in which B is a phenyl ring substituted with a single substituent selected from C$_{1-4}$ alkyl, C$_{1-4}$ alkoxy and halogen.

5. A compound of the formula

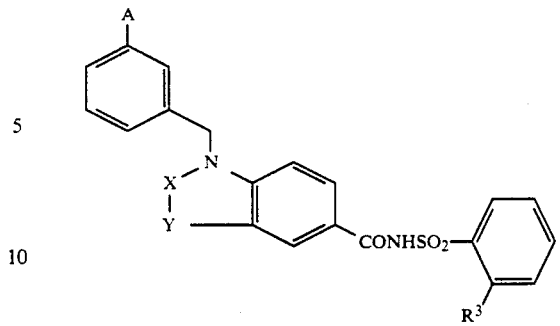

in which A is —NHCOR$^1$, —NHCOOR$^1$, —NHCSNHR$^1$ or —NHCONHR$^1$, —X—Y— is —CH=CH— or —CH$_2$—CH$_2$—, R$^1$ is benzyl, C$_{1-4}$ alkyl or halo-substituted C$_{1-4}$ alkyl and R$^3$ is C$_{1-4}$ alkyl, C$_{1-4}$ alkoxy or halogen.

6. A method of treating an animal suffering from or susceptible to a disease in which leukotrienes are a causal mediator which comprises administering an effective amount of a compound according to claim 1, or a pharmaceutically-acceptable salt thereof.

7. The method of claim 6 wherein the animal is a human.

* * * * *